(12) United States Patent
Wimplinger

(10) Patent No.: US 10,109,538 B2
(45) Date of Patent: Oct. 23, 2018

(54) MEASURING DEVICE AND METHOD FOR MEASURING LAYER THICKNESSES AND DEFECTS IN A WAFER STACK

(75) Inventor: Markus Wimplinger, Ried im Innkreis (AT)

(73) Assignee: EV Group E.Thallner GmbH, St. Florian am Inn (AT)

(*) Notice: Subject to any disclaimer, the term of this patent is extended or adjusted under 35 U.S.C. 154(b) by 249 days.

(21) Appl. No.: 13/883,777

(22) PCT Filed: Nov. 12, 2010

(86) PCT No.: PCT/EP2010/006902
§ 371 (c)(1), (2), (4) Date: May 7, 2013

(87) PCT Pub. No.: WO2012/062343
PCT Pub. Date: May 18, 2012

(65) Prior Publication Data
US 2013/0228015 A1 Sep. 5, 2013

(51) Int. Cl.
| | |
|---|---|
| H01L 21/66 | (2006.01) |
| G01B 7/06 | (2006.01) |
| G01B 11/06 | (2006.01) |
| G01B 17/02 | (2006.01) |
| G01N 29/04 | (2006.01) |

(Continued)

(52) U.S. Cl.
CPC .............. *H01L 22/20* (2013.01); *G01B 7/06* (2013.01); *G01B 11/0625* (2013.01); *G01B 17/02* (2013.01); *G01B 17/025* (2013.01); *G01N 29/043* (2013.01); *G01N 29/265* (2013.01); *G01N 29/27* (2013.01); *G01N 29/275* (2013.01); *H01L 21/67253* (2013.01); *H01L 22/12* (2013.01); *G01N 21/9501* (2013.01); *G01N 21/9505* (2013.01); *G01N 2291/0231* (2013.01); *G01N 2291/0289* (2013.01);

(Continued)

(58) Field of Classification Search
CPC ....................................................... G01B 17/02
USPC .............................................................. 73/632
See application file for complete search history.

(56) References Cited

U.S. PATENT DOCUMENTS 4,366,713 A * 1/1983 Gilmore ................ G01N 29/11 73/588
5,029,476 A * 7/1991 Metala et al. .................. 73/620

(Continued)

FOREIGN PATENT DOCUMENTS

| CA | 2 314 305 | 1/2002 | ............ G01B 17/00 |
| CN | 100578145 C | 1/2010 | ............ G01B 17/02 |

(Continued)

OTHER PUBLICATIONS

Document XX-000907059, "Thickness Measurements of Epitaxial Layers of Double Epitaxial Silicon Wafers by Far-Infrared Reflection"; Shirai et al., May 1998, pp. 1720-1723.

(Continued)

*Primary Examiner* — Son T Le
*Assistant Examiner* — Tarun Sinha
(74) *Attorney, Agent, or Firm* — Kusner & Jaffe

(57) ABSTRACT

The invention relates to a measurement means and a method for measuring and/or acquiring layer thicknesses and/or voids of one or more layers of a wafer stack on a plurality of measuring points distributed on the wafer stack and a corresponding wafer processing device.

19 Claims, 5 Drawing Sheets

(51) Int. Cl.
  *G01N 29/265* (2006.01)
  *G01N 29/27* (2006.01)
  *G01N 29/275* (2006.01)
  *H01L 21/67* (2006.01)
  *G01N 21/95* (2006.01)

(52) U.S. Cl.
  CPC .............. *G01N 2291/02854* (2013.01); *G01N 2291/044* (2013.01); *G01N 2291/2697* (2013.01); *H01L 21/67288* (2013.01)

(56) References Cited

U.S. PATENT DOCUMENTS

| | | | |
|---|---|---|---|
| 5,119,678 A | 6/1992 | Bashyam et al. ............... 73/602 |
| 5,392,113 A | 2/1995 | Sayka et al. .................. 356/237 |
| 6,078,397 A * | 6/2000 | Monchalin et al. ........... 356/503 |
| 6,180,497 B1 * | 1/2001 | Sato .................... H01L 21/0203 |
| | | | 257/E21.216 |
| 6,234,025 B1 | 5/2001 | Gieske et al. .................. 73/642 |
| 6,237,025 B1 | 5/2001 | Ludwig et al. ............... 709/204 |
| 6,611,064 B1 * | 8/2003 | Kousaka ............. H01L 23/3121 |
| | | | 257/100 |
| 6,656,755 B1 | 12/2003 | Ohkawa .......................... 438/16 |
| 6,704,101 B1 | 3/2004 | Rangarajan et al. ...... 356/237.2 |
| 6,754,305 B1 | 6/2004 | Rosencwaig et al. .......... 378/89 |
| 6,774,989 B1 * | 8/2004 | Rangarajan et al. ...... 356/237.2 |
| 6,948,370 B2 * | 9/2005 | Chatellier .............. G01N 19/04 |
| | | | 427/8 |
| 7,110,097 B2 | 9/2006 | Meeks et al. .................... 356/73 |
| 7,661,315 B2 * | 2/2010 | Busch ............... H01L 21/67288 |
| | | | 73/618 |
| 7,738,113 B1 | 6/2010 | Marx et al. .................... 356/496 |
| 2002/0048844 A1 | 4/2002 | Sakaguchi .................... 438/106 |
| 2004/0121618 A1 * | 6/2004 | Moore .................. C09J 193/04 |
| | | | 438/782 |
| 2005/0119678 A1 | 6/2005 | O'Brien et al. ............... 606/159 |
| 2006/0066854 A1 | 3/2006 | Meeks et al. ................. 356/369 |
| 2006/0072126 A1 | 4/2006 | Meeks .......................... 356/630 |
| 2006/0150736 A1 | 7/2006 | Akamatsu ....................... 73/579 |
| 2006/0234025 A1 | 10/2006 | Myard et al. .............. 428/292.1 |
| 2007/0148792 A1 | 6/2007 | Marx et al. ..................... 438/14 |
| 2007/0179659 A1 * | 8/2007 | Vandamme ............. B24B 7/228 |
| | | | 700/164 |
| 2007/0238805 A1 * | 10/2007 | Maeda ............... C08G 18/6266 |
| | | | 522/109 |
| 2008/0021673 A1 | 1/2008 | Blander et al. ................ 702/171 |
| 2008/0087113 A1 * | 4/2008 | Bagley .................... G01H 9/008 |
| | | | 73/865.8 |
| 2008/0126014 A1 | 5/2008 | Cui et al. ....................... 702/189 |
| 2009/0196489 A1 | 8/2009 | Le ................................. 382/148 |
| 2009/0218560 A1 | 9/2009 | Flaim et al. ....................... 257/9 |
| 2010/0177312 A1 | 7/2010 | Fujimori et al. ............... 356/364 |
| 2010/0182592 A1 | 7/2010 | Dall'Aglio ....................... 356/51 |
| 2011/0224819 A1 * | 9/2011 | Kang et al. .................... 700/108 |

FOREIGN PATENT DOCUMENTS

| | | | | |
|---|---|---|---|---|
| DE | 195 25770 C1 | 8/1996 | ............ G01N 21/95 |
| EP | 0 416 245 A2 | 3/1991 | ............ G01B 17/00 |
| FR | 2 864 339 A1 | 6/2005 | ............ G01N 21/88 |
| JP | H02-170008 A | 6/1990 | ............ G01B 11/06 |
| JP | H 05187856 A | 7/1993 | ............ G01B 17/02 |
| JP | H 07161596 A | 6/1995 | ............ H01L 21/02 |
| JP | H 07190747 A | 7/1995 | ............ G01B 17/04 |
| JP | H 10229108 A | 8/1998 | ............ G01B 11/02 |
| JP | 0159932 B1 | 3/1999 | ............ G01B 17/00 |
| JP | 2000-310512 A | 11/2000 | ........... B24B 37/013 |
| JP | 2001-226586 A | 8/2001 | ............. B05D 7/00 |
| JP | 2001-349715 A | 12/2001 | ............ G01B 11/30 |
| JP | 2006-189380 A | 7/2006 | ............ G01N 29/06 |
| JP | 2007-199013 A | 8/2007 | ............ B24B 49/02 |
| JP | 2008-083059 A | 4/2008 | ............ G01B 11/00 |
| JP | 2008-139177 A | 6/2008 | ............ G01B 11/06 |
| JP | 2009-216531 A | 9/2009 | ............ G01B 11/24 |
| JP | 2010-164403 A | 7/2010 | ............ G01B 17/02 |
| JP | 2012-042431 A | 3/2012 | ............ G01N 19/04 |
| TW | 201000888 A | 1/2010 | ........... G01N 21/956 |
| WO | WO 2005/064320 A1 | 7/2005 | ............ G01N 21/88 |

OTHER PUBLICATIONS

Document XX 000656397, "Ultrasonic Multilayer Metal Film Metrology," Morath et al., Jun. 1997, 4 pages.
Int'l Search Report from corresponding PCT/EP2010/006902 (Form PCT/ISA/210); 3 pages (English version only).
Office Action received in corresponding European Patent Application No. 10790722.2-1554, dated Jan. 27, 2015.
Shuangwu et al.: "Temporary Bonding of Wafer to Carrier for 3D-Wafer Level Packaging", Electronics Packaging Technology Conference, 2008. EPTC 2008. 10TH, IEEE, Piscataway, NJ, USA, Dec. 9, 2008, Seiten 405-411, XP031413839, ISBN: 978-1-4244-2117-6.
Office Action received in corresponding Chinese Patent Application No. 201080070098.8, dated Oct. 27, 2014 (English-language translation provided).
Non-Patent Reference cited in Chinese Office Action dated Oct. 27, 2014: Article written by C.J. Morath and G.J. Collins, entitled "*Ultrasonic Multilayer Metal Film Metrology*" (Solid State Technology, Jun. 1997, vol. 40, Issue 6, p. 85).
Office Action issued in connection with related U.S. Appl. No. 15/053,237 dated Jul. 26, 2016.
Office Action issued in corresponding Japanese Patent Application No. 2015-134456 dated May 30, 2016.
Office Action issued in corresponding Korean Patent Application No. 10-2013-7008189 dated Jun. 2, 2016.

* cited by examiner

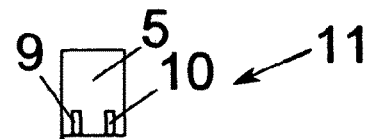
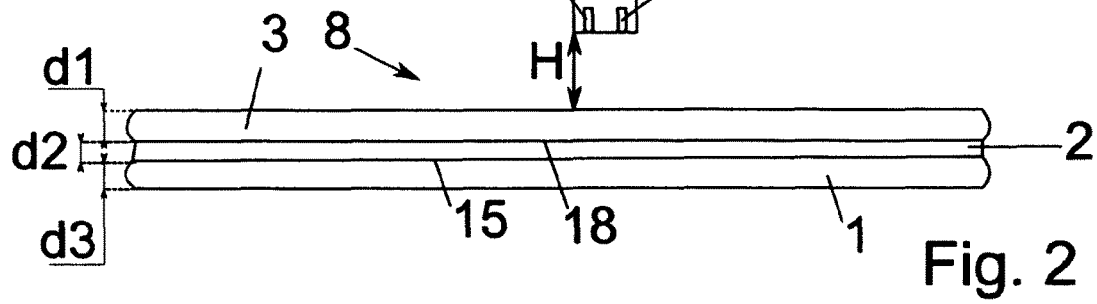
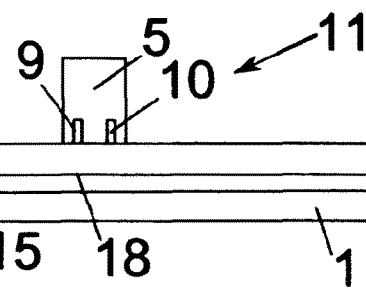
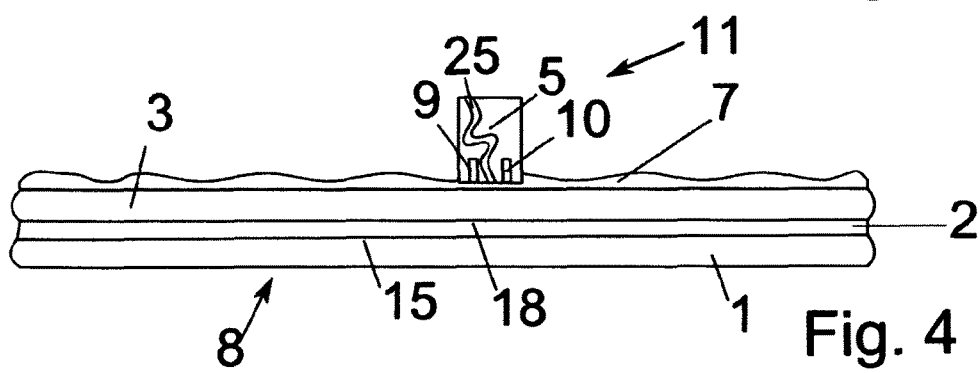
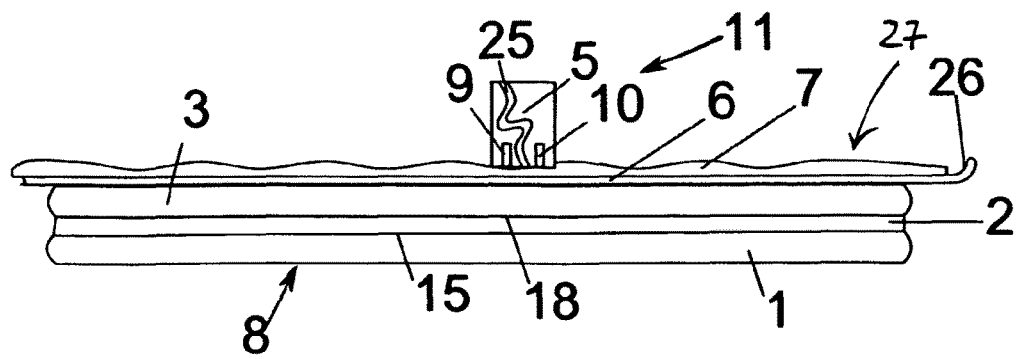

MEASURING DEVICE AND METHOD FOR MEASURING LAYER THICKNESSES AND DEFECTS IN A WAFER STACK

FIELD OF THE INVENTION

This invention relates to a measuring device for measuring layer thicknesses and/or detecting voids of one or more layers of a wafer stack on a plurality of measuring points which are distributed on the wafer stack. Furthermore this invention relates to a wafer processing device for processing a wafer stack and a method for measuring layer thicknesses and/or detecting voids of one or more layers of a wafer stack at a plurality of measuring points which are distributed on the wafer stack.

BACKGROUND OF THE INVENTION

Development in the semiconductor industry is currently in the direction of wafer bonding processes becoming increasingly important. Thus for example novel functions such as motion sensors and/or orientation sensors in cell phones and other portable devices such as game consoles are leading to a rapidly increasing demand for microelectromechanical (MEMS) components which can detect acceleration and rotational speeds.

Another field with rapid growth is components which are produced as so-called 3D ICs. They include a chip system which consists of several layers with transistors ("active layers") which are connected among one another by means of contacts which lead through the silicon. These plated-through holes are called "through silicon vias" or abbreviated "TSVs" in the industry.

In order to produce these TSVs as economically as possible, as well as to be able to implement other desired advantages such as a small overall packing size, it is necessary to thin the wafers to a suitable size before or after the TSV production or in the course of TSV production. Accordingly it is now distinguished between so-called via first, via middle and via last processes. With respect to thinning of the wafers, it has been found that the desired target thicknesses are no longer sufficient to be able to reliably move the wafer from one process step to the next since the mechanical stability of the wafer, especially in the currently conventional 300 mm wafer, is no longer extant.

Wafers are therefore advantageously temporarily mounted on a carrier so that reliable handling of the thin wafer, which conventionally has a thickness <150 µm, but usually <100 µm and often <80 or even <50 µm, is ensured. After completing the necessary process steps the wafer s again detached from the carrier. These two methods are called temporary bonding and debonding.

In a first process step, the product wafer is bonded onto the carrier by means of suitable bonding technology which is known to one skilled in the art. This bonding step generally takes place such that the first main surface of the product wafer on which the chip structures are built up is oriented such that this surface comes into contact with the temporary adhesive and this adhesive layer subsequently produces the contact with the carrier wafer.

In almost all cases, within the framework of this rear side processing however mechanical thinning of the product wafer takes place. This includes especially grinding steps in which a defined thickness of the product wafer is removed by grinding. Conventionally, in this connection individual grinding steps with different grinding rates and/or grain sizes of the grinding wheels are used. Generally there are a first grinding step with a higher material removal rate (coarse grinding) and a second grinding step with a lower material removal rate (fine grinding).

In order to ensure the quality of the final chips and the integrity of the temporarily bonded wafer in conjunction with the rear side process steps, it is necessary for the temporary adhesive connection to satisfy certain quality criteria. In this connection, there are a host of requirements for the adhesive material which are known to one skilled in the art. They relate among others to the capacity of the adhesive to be able to tolerate certain process conditions which can arise during rear side processing. They include among others temperature stability, compatibility with a vacuum environment (no outgassing), stability of the adhesive relative to chemicals such as solvents, acids, and bases, compatibility with diverse mechanical loads or electromagnetic waves (for example irradiation with light of a certain wavelength) and various combinations of these parameters. In addition to the demands on the adhesive material, there is also a host of parameters which relate to the geometrical and mechanical integrity of the adhesive layer. In particular it is of enormous importance for the success of rear side processing that the adhesive layer has a precisely defined and reproducible thickness, and no voids.

In contrast to thinning of an individual wafer however in the case of a temporarily bonded wafer the carrier wafer and the adhesive layer are located between the wafer support and the grinding means (grinding wheel, etc.). Thus the thickness of the carrier wafer and the adhesive layer together influences the uniformity of the final thinned product wafer.

Therefore, it can be stated in summary that it is necessary to be able to precisely control and monitor the uniformity of the thickness of the adhesive layer and generally also the absolute thickness value in a production process. For certain cases, depending on the control of the grinding process it can also be necessary to know the thickness of the carrier wafer—under certain circumstances also that of the entire temporarily bonded stack. In any case, it is, however, necessary to ensure a corresponding quality of the adhesive layer with respect to the uniformity of the thickness and optionally the absolute thickness value.

With respect to the voids, it holds that during a grinding process and possible subsequent polishing process they would lead to the wafer being inadequately mechanically supported, and in this way damage of the wafer or at least nonuniformities of the wafer thickness which is desired during thinning can occur. This nonuniformity is caused by the mechanical flexibility of the base which is formed by these voids. In other words, the wafer would for example bend/sag into these voids during grinding and thus less substantial removal would take place at these sites; this would subsequently result in a locally elevated thickness of the thinned wafer. This effect would be stronger, as the target thickness of the thinned wafer becomes smaller since it becomes more flexible with decreasing thickness. Ultimately this can even lead to fracture of the wafer during thinning. These fracture events constitute a major risk for grinding and/or polishing processes since the resulting relatively large material pieces can entail further damage to the entire wafer, but also of the grinding wheels and/or the polishing device. Aside from these problems, during grinding and/or polishing these voids can also lead to faults during the remaining rear side process steps. It should be noted here only as an example that gases enclosed in these voids during process steps which occur in vacuum chambers can lead to the thinned silicon wafers bursting during these process steps at these sites. In addition to the loss of the chip located at this site this would also result in further problems since the resulting particles would contaminate the system used in which the bursting took place, and under certain circumstances other production units and possibly would also entail quality problems on other wafers which have been processed on this unit.

SUMMARY OF THE INVENTION

The object of this invention is therefore to optimize the quality criteria such as the absence of voids, the reproducibility and uniformity of the adhesive thickness and to ensure as little scrap as possible in the production or processing of temporarily bonded wafer stacks.

This object is achieved with the features of the claims. Advantageous developments of the invention are given in the dependent claims. All combinations of at least two of the features given in the specification, the claims and/or the figures also fall within the framework of the invention. At the given value ranges, values within the indicated limits will also be disclosed as boundary values and will be claimed in any combination.

The basic idea of this invention is on the one hand to recognize, in the processing of wafers, deviations relative to the aforementioned quality criteria at a time as early as possible in order to minimize any loss of product wafers for this reason. This can be ensured especially in that the layer thickness of individual layers of the wafer stack are measured and/or voids of individual layers of the wafer stack are detected, and especially close in time before the wafer stack is ground. It is especially important to monitor the geometrical parameters of the carrier wafer since it is used for mechanical support of the product wafers and during the grinding process comes to rest between the wafer support, which can be used as reference plane or reference surface, and the grinding wheel. Close in time in the aforementioned sense means that in the processing chain of wafer stacks there are as few wafer stacks as possible in the processing chain before the indicated wafer stack, therefore between the measurement step and/or detection step and the grinding step, especially a maximum of five, preferably a maximum of three, even more preferably a maximum of one. It can be provided as claimed in the invention that the measurement step and/or detection step is carried out in a measurement and/or detection module (also metrology module) and the grinding step is carried out separately in space in an especially adjacent grinding module. The measurement step and/or detection step and the grinding step take place in-line as claimed in the invention. It can also be that the examination of the wafer stack has been completed before the previous wafer has been completely ground, and, therefore, is still in the grinding module. The measured and/or detected wafer stack must then "wait" until it can advance.

On one especially advantageous embodiment, the measurement step and/or detection step takes place close in time to the temporary bonding step. This results in that in the case of faults, which occur in the temporary bonding step, the amount of misprocessed material is reduced. This offers the advantage that the amount of material, especially the number of bonded wafer stacks, which must be supplied to reworking can be reduced; this entails economical and logistical advantages. In this connection, close in time means that the measurement and/or detection takes place in any case before grinding of the wafer. As already stated, the grinding process constitutes an irreversible process which can lead to catastrophic faults and especially to a total loss of individual bonded wafer stacks. But close in time advantageously means that a maximum of 10 further wafer stacks have been bonded before the inspection of a given wafer stack has taken place. It is still better if this number can be reduced to less than 7 or still better 5 or 3. These numbers relate to a process sequence in which all bonded wafer stacks after the temporary bonding process, especially directly (immediately) after the temporary bonding step, are supplied to the measurement step and/or detection step as claimed in the invention. This just described reduction of these wafer stacks which are waiting for the inspection step in the process sequence can be advantageously achieved by means of a configuration of the production environment in which the device that executes the temporary bonding step is located as near as possible in space to the measuring device, as claimed in the invention. In particular, this can be achieved by integrating the measuring device into a temporary bonding device. This integrated approach is conventionally called "in-line integration" or "in-line metrology" in industry. This can be implemented according to this invention in combination with any temporary bonding approaches which are known from the prior art. For example, it is also conceivable to integrate the measuring device into a temporary bonding unit for thermoplastic or UV-curable adhesives, these units conventionally containing one or more coating modules for the application of the adhesive and one or more bond modules between which the wafers to be processed are moved by means of an automatic wafer handling device which is especially part of the unit. Depending on the type of adhesive used, heating modules can also be additionally integrated in the system and are used to drive the solvent out of the adhesive layer. It is also advantageously conventional to integrate suitable alignment devices known to one skilled in the art for aligning the wafers into these systems.

In addition, one basic idea of the invention comprises detecting voids in the adhesive layer and measuring the adhesive layer thickness and possible fluctuations of this adhesive layer thickness.

Another aspect of the invention is that the acquired values can be automatically evaluated as data in order to automatically make a decision about further processing or removal of the wafer from the process chain.

Another central aspect of the invention comprises integrating the subject matter of the invention into an automatic processing device for the temporary bonding of product wafers. In this way an analysis as complete as possible of each product wafer will be enabled without reducing the productivity rate of the processing device. Detection and/or measurement thus takes place "in-line," therefore as "in-line metrology." Accordingly, it is provided according to one embodiment of the measuring device as claimed in the invention that it can be used in a wafer processing system, especially in-line.

In accordance with the present invention, there is provided a module-like structure comprised of process modules which are located in-line for the process sequence or the process chain. Use in conjunction with the following modules in a wafer processing system is especially advantageous:

a painting module for at least partial painting of the wafer stack, especially with an adhesive, advantageously with a temporary adhesive, a bond module for connecting the wafer layers of the wafer stack, a measuring device as claimed in the invention in an inspection module, a handling means, especially with one or more robot arms, for transport of each wafer stack within the wafer processing system from one module to the next, and optionally, a heating means for driving out the solvent.

If deviations are detected in this connection especially before rethinning of the product wafer, it is possible to subject the product wafer or the wafer stack to a rework. This is constituted especially such that the product wafer would be again detached from the carrier and the entire temporary bonding process could be carried out again. For this detachment step, systems which are intended specifically for this purpose or in-line modules can be used. In particular, debonding systems are especially suitable for this purpose and they are conventionally used for detaching the thin product wafer from the carrier. Optionally, process parameters designed for this purpose for this debonding system can be adapted to the requirements of debonding of a product wafer which has not been thinned or which has not been completely thinned. This rework process is of great importance for purposes of cost-effective production. In particular, product wafers or wafer stacks which have a very high degree of complexity, which can be expected for these 3D IC wafer stacks, have a very considerable value in this stage since they have already progressed far in the production flow. The value of these wafer stacks generally exceeds 1000 euros, in part even 10,000 euros. Therefore it is decisive, as claimed in the invention, to detect n time or as early as possible so-called catastrophic faults which would lead to a total loss of the wafer stack and to supply them to a rework process before the wafer stacks pass through a process step after which this rework process would no longer be possible. In this respect, the grinding of the wafer stack for reducing the thickness can be regarded in any case as a step after which this rework process would no longer be possible and otherwise would threaten a total loss of the product wafer.

To the extent the measuring device is made to work without mechanical action on the wafer stack, especially with a distance H from the wafer stack, the measurement and/or detection can take place especially carefully by the measuring device, preferably without contact. When using ultrasonic waves, the contact necessary for propagation of the ultrasonic waves takes place between the wafer stack and the measuring device via a fluid agent which is provided on the wafer stack and which is suitable for transmission of ultrasonic waves. In this case, according to one preferred version, a separator, especially a membrane, is provided between the fluid agent and the wafer stack for shielding of the wafer stack from the liquid. The separator must be suitable for transmission of ultrasonic waves. The space underneath the membrane can preferably be evacuated so that the membrane rests as uniformly and flat as possible on the wafer stack. The use of a negative pressure is indispensable since only the ambient pressure provides for the membrane to completely cling to the wafer stack. If this were not so, air-filled cavities could adulterate the measurement result since air would at least largely reflect acoustic waves.

According to one advantageous embodiment of the invention, it is provided that the measuring device, especially the transmitter and receiver, can be used at the same time for measuring layer thicknesses and detecting voids, especially with a layer resolution of <10 µm, preferably <1 µm, even more preferably <0.1 µm. As claimed in the invention, it is moreover conceivable to use several transmitter/receiver units at the same time, especially located next to one another, in order to be able to scan the surface correspondingly more quickly. The layer resolution is meant in the transverse direction to the reference plane R, therefore depth resolution or vertical resolution or thickness resolution.

The diameter D of the measurement signal is advantageously between 1 µm and 100 µm, preferably between 5 µm and 50 µm, and more preferably between 10 µm and 30 µm. For a laser beam, the aforementioned diameter D corresponds for example to the diameter of the laser beam.

In another advantageous embodiment of the invention, it is provided that adjacent measuring points can be measured by the measuring device within a reference plane R with a distance X and Y of less than 5 mm, preferably less than 3 mm, even more preferably less than 1 mm, most preferably less than 0.5 mm. Therefore blanket, grid-like sensing of the entire wafer stack takes place so that essentially all voids can be detected as seamlessly as possible.

Width resolution of the measurement signal in the lateral direction, therefore parallel to the reference plane R, is advantageously between 0.1 µm and 50 µm, preferably between 1 µm and 30 µm, and more preferably between 10 µm and 20 µm. A laser beam is intended to take measurements for example at a certain measuring point. It will however not hit the measuring point exactly, but will deviate by deltaX/deltaY. Here deltaX and deltaY correspond to the width resolution. With width resolution especially the extension, therefore width or diameter of a void, is detected. The better the width resolution, the more measurements must be taken. Therefore, as much as possible an optimum must be set between rapid measurement and/or detection of as many voids as possible. The thinner the target thickness of the wafer or wafer stack, the more critical small voids already are.

According to one preferred embodiment of the invention, it is provided that the measurement and/or detection is two-stage, especially by a first high-speed and coarse measuring device and an optional second, very precise measuring device. Only wafer stacks which have been rated as possibly critical in the first measuring device pass through the second measuring device. The second measuring device is not provided in-line so that as much as possible the process flow is not disrupted. A wafer stack which is possibly rated as critical in the first measuring device by the evaluation unit is therefore at least temporarily separated from the process sequence.

The relationship between the point grid distance, the diameter D of the measurement signal and the width resolution is shown in FIG. 9.

This method can be used in situ and/or in-line. In-situ means the use of the method during a technological/physical/chemical processing step. Here for example the rethinning of a structure wafer or the edge zone etching in a chemical bath should be named.

Inline is defined as the use of the method in a process module which is upstream or downstream of another process module. In one embodiment, the first module can be a bonding station, as claimed in the invention. The following module would then, in this case in a typical embodiment, be the measuring device which has been described here in order to measure a wafer stack. While a wafer stack is bonded in the bonding station, in the measurement station one of the wafer stacks bonded beforehand, advantageously a wafer stack which was bonded beforehand as close in time as possible, according to the aforementioned explanations for the term close in time, especially a wafer stack bonded immediately beforehand, is measured and/or sensed. In-line therefore differs from in-situ in that a separation of the method as claimed in the invention takes place into its own module which however has been system-integrated into a processing chain with other processing steps.

Advantageously, it is furthermore provided that the measuring device as claimed in the invention is provided with a preferably fixed interferometer which is mechanically coupled especially to the transmitter and the receiver, especially white light interferometer, for measuring its distance to one surface on at least one of the measuring points.

The aforementioned features which have been described for the measuring device apply accordingly to the device as claimed in the invention and the method as claimed in the invention.

BRIEF DESCRIPTION OF THE DRAWINGS

Other advantages, features and details of the invention will become apparent from the following description of preferred exemplary embodiments and using the drawings.

FIG. 1 shows a measuring device as claimed in the invention in a first embodiment, FIG. 2 shows a measuring device as claimed in the invention in a second embodiment, FIG. 3 shows a measuring device as claimed in the invention n a third embodiment, FIG. 4 shows a measuring device as claimed in the invention in a fourth embodiment.

DETAILED DESCRIPTION OF PREFERRED EMBODIMENTS

The same components and parts with the same action are identified with the same reference numbers in the figures.

Figure 8:
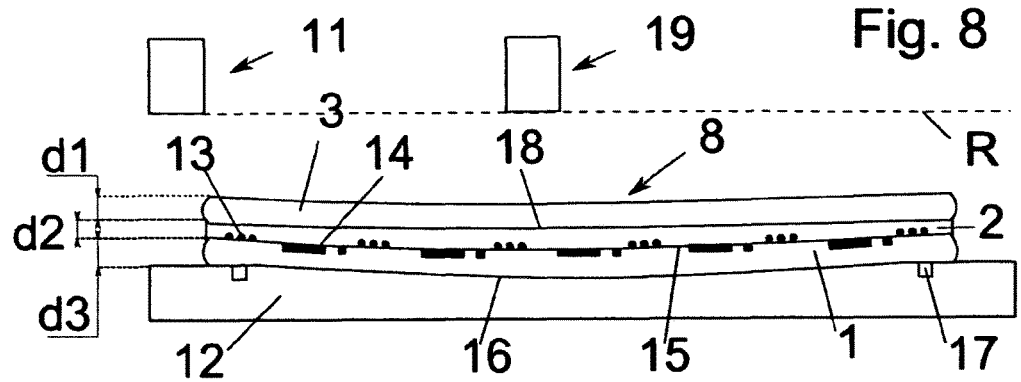
FIG. 8 shows a schematic of a device as claimed in the invention for processing of a wafer stack.
Figure 9:
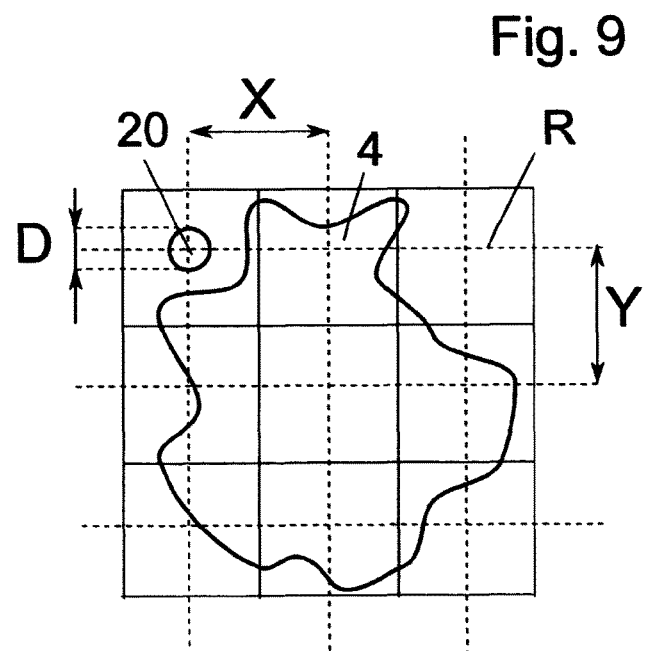
FIG. 9 shows a schematic of the detection of a void of a wafer stack.

FIG. 8 shows a wafer processing device as claimed in the invention for processing of a wafer stack 8. Wafer stack 8 is comprised of one structure wafer 1, one connecting layer 2 and one wafer 3. The structure wafer 1 at a transition 15 between the structure wafer 1 and the connecting layer 2 has contacts 14 which have been introduced into the surface of the structure wafer 1 and bumps 13 which project from the surface and which can consist of metal alloys. The structure wafer 1 can also be made without structures, in the same way as the wafer 3 can be made with structures.

The wafer stack 8 is fixed, its flat side opposite the surface of the structure wafer 1, on a surface 16 of a mount 12, here a chuck. Fixing takes place via vacuum paths 17 of the mount 12.

The connecting layer 2 is made as temporary adhesive and by means of the latter the structure wafer 1 is temporarily bonded onto the wafer 3. A further transition 18 is accordingly between the connecting layer 2 and the wafer 3.

The device furthermore has a measuring device 11 which can move relative to the wafer stack 8 along a reference plane R. The performance of relative motion is decisive so that a movement of the wafer stack 8, especially by moving the mount 12, is likewise conceivable. Here it is decisive that the relative motion between the measuring device 11 and the wafer stack 8 can be sensed, for example in a X-Y coordinate system which spans the reference plane R.

Figure 5:
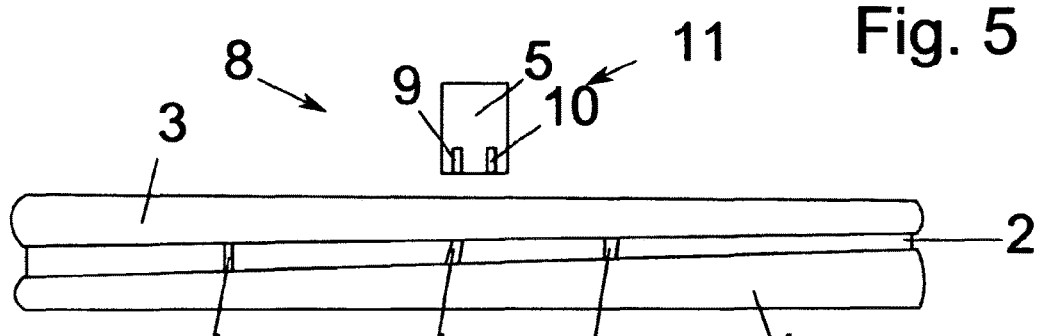
FIG. 5 shows an illustration of possible quality defects of a wafer stack.

The operation of the measuring device 11 is shown in different versions in FIGS. 1 to 4. FIG. 5 shows the possible problems which can arise in the joining of wafers 1, 3. For example, the connecting layer 2 can have a nonuniform layer thickness. In the ideal case the wafers 1, 3 would be equally thick everywhere. FIG. 5 shows that the wafers 1, 3 can also have a nonuniform thickness distribution. Furthermore, the wafers 1, 3 can have so-called "voids" 4.

According to FIG. 1, the measuring device 11 is comprised of a housing 5 in which on its bottom there are a transmitter 9 and a receiver 10. They are aligned in the direction of the wafer stack 8, especially parallel to the reference plane R. The measurement is based on waves being injected into the bonded wafer stack 8 by means of the transmitter 9 and on the reflections on the individual transitions 15, 18 between the different materials being acquired with the receiver 10. The receiver 10 is made as a signal detector for detection of the signals in the form of electromagnetic waves or ultrasonic waves.

In particular, electromagnetic waves with a suitable wavelength at which there is sufficient transparency of the wafers 1, 3 used and of the adhesive material of the connecting layer 2 are suitable as signal waves. For silicon wafers this can be for example light in the infrared range or x-radiation. For glass wafers light in the visible range and when using suitable glasses also in the UV range would be suitable.

The signal source for the electromagnetic radiation can be located especially in the housing 5, especially integrated in the transmitter 9. As an alternative to electromagnetic waves, acoustic waves are suitable, especially waves in the ultrasonic range from 100 kHz to 800 MHz, preferably 100 MHz to 400 MHz.

The use of a light source with electromagnetic radiation in the infrared range, especially 1050 nm to 10 µm, preferably 1300 nm light wavelength, is preferred. The optics of the measuring device is designed such that the beam of electromagnetic waves can be focused and routed onto the wafer stack 8.

To the extent the transmitter 9 and the receiver 10 or the housing 5, as in the exemplary embodiments according to FIGS. 2, 3 and 4, are in direct contact with the wafer stack 8 or a liquid 7 which has been applied to the wafer stack 8, measurement and/or sensing takes place by contact coupling. This type of contact coupling takes place mainly when ultrasonic waves are used.

When using electromagnetic waves there is a distance H between the transmitter-receiver unit and the wafer stack 8.

In the case of the ultrasonic measurement shown in FIG. 3 by means of the liquid 7, it is applied to the wafer stack 8 before the measurement and the housing 5 with the ultrasonic transmitter is immersed into the liquid 7 in order to transmit the ultrasonic waves to the wafer stack 8 and to enable a measurement by the transmitter 9 and the receiver 10. The transmitter 9 can be made here as an ultrasonic transmitter. The liquid 7 is generally applied through the housing 5. The housing 5 has a feed line 25 via which the especially continuous inflow of liquid 7 from a liquid reservoir takes place.

In the embodiment according to FIG. 4 it is moreover provided that between the liquid 7 and the wafer stack 8 there is a membrane 6 to protect the wafer stack 8 from the liquid 7. The membrane 6 is so elastic that it can be matched to the topography of the surface of the wafer stack 8. The liquid 7 is applied to the surface of the membrane 6. The measurement signal is then injected through the liquid and through the membrane 6 into the wafer stack 8. The space underneath the membrane 6 can preferably be evacuated and is evacuated before the measurement takes place. Evacuation has the advantage that the air pressure on the side of the housing 5 presses the membrane 6 onto the surface of the wafer 3. This ensures that the membrane covers the surface of the wafer 3 without forming cavities and thus signal injection takes place only via solids and/or liquids, especially without a gaseous phase.

In one especially advantageous version of the embodiment according to FIG. 4, the membrane 6 is used as a liquid reservoir by a trough-shaped liquid reservoir 27 being formed by a peripheral membrane wall 26. In this special embodiment it is therefore conceivable for there to be a closed circuit between the liquid reservoir 27 and the feed line 25. In this way, a very clean execution of the measurement and/or sensing is possible.

In one especially preferred embodiment it is also conceivable for the device to contain only the trough-shaped liquid reservoir 27 with respect to liquid handling and for a circuit for the liquid to be completely omitted, especially at least during the measurement process. The feed and drainage of the liquid to and/or from the liquid reservoir 27, which drainage is intended optionally, in particular for facilitating maintenance efforts, take place in this case by suitable means which are not shown in the figures for liquid supply and liquid discharge.

The signals reflected on the transitions 15, 18 and on the mount surface 16 in the form of electromagnetic waves or ultrasonic waves are evaluated by means of one suitable receiver 10 at a time and with consideration of the propagation velocity of the waves in the various materials of the structure wafer 1, the connecting layer 2 and the wafer 3 allow a precise conclusion about the material thicknesses d1 of the wafer 3 or d2 of the connecting layer 2 and d3 of the structure wafer 1. Thus precise detection of the thicknesses and the thickness uniformity of the layers of the wafer stack 8, therefore of the structure wafer 1, the connecting layer 2 and of the wafer 3 is possible. By moving the measuring device over the entire wafer stack 8 parallel or along the reference plane R the layer thicknesses can be determined at the corresponding measuring points with local resolution.

As described above, for measuring and/or sensing of the wafer stack 8 motion relative to the transmitter 9 and the receiver 10 takes place. This can be achieved either by moving the wafer stack 8 or the transmitter-receiver unit or a combination of the two movement possibilities. Preferably an arrangement is chosen in which as few axes as possible are required, especially by a travelling means for moving the wafer stack along one X and one Y-axis, therefore parallel to the reference plane R. The measuring device is preferably rigidly mounted.

Figure 6A:
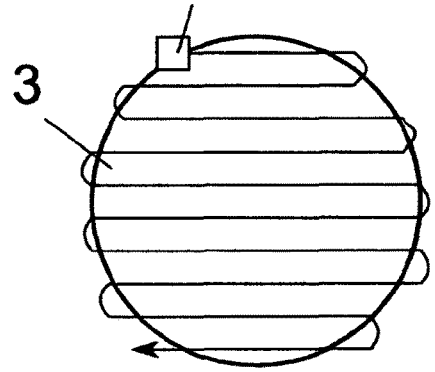
FIGS. 6a-6c show different method sequences as claimed in the invention for measuring and/or sensing several measuring points.
Figure 6B:
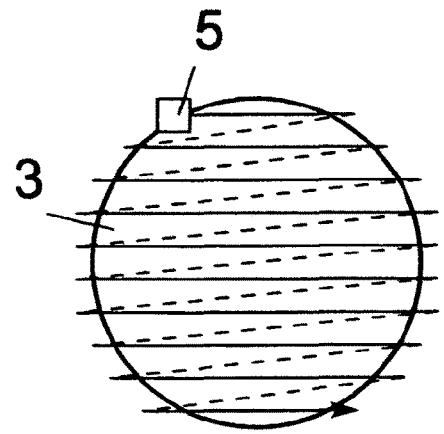
Figure 6C:
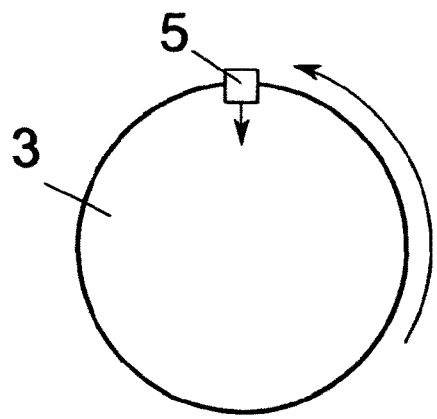

In FIGS. 6a to 6c the most important scanning methods for sensing the entire wafer stack 8 are shown, in FIG. 6a sensing taking place in a meander form. Meandering scans have the advantage that the sensing distance can be very quickly traversed. Another type of scanning is a line scan according to FIG. 6b. This type of scan can be accomplished by a linear drive, possible play of translation units of the linear drive, especially reverse play, being minimized. This version is particularly advantageous especially in the above described two-stage measurement method, particularly in the second measuring device. Another alternative consists in constant advance of the housing 5 with the wafer stack 8 rotating toward the center of the wafer stack 8. This yields helical sensing. It is common to the aforementioned scan methods that the scanning takes place continuously. The continuous measurement signals of the individual measuring points are converted and evaluated accordingly by an evaluation unit. The time for scanning of one wafer stack, especially for an in-line, integrated measuring device as claimed in the invention, is less than 180 seconds, preferably less than 100 seconds, more preferably less than 60 seconds. For a measuring device that is not integrated in-line and provided especially in addition to a measuring device which is integrated in-line, especially a measuring device that is used for detailed inspection of especially separated wafer stacks, the inspection times can also be much longer. It is quite conceivable for these measurement processes to last longer than 10 minutes, in many cases even longer than 20 minutes or 30 minutes.

Figure 10:
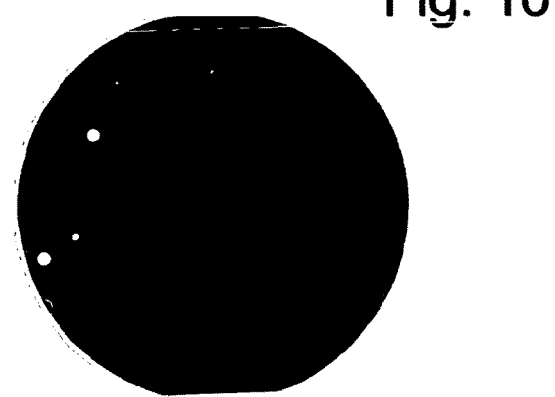
FIG. 10 shows a photograph of a wafer stack which has been sensed by ultrasonic signals with the measuring device as claimed in the invention.

If there are voids 4 in the adhesive layer 2 (FIG. 7a), within this void 4 relaying the injected wave is either not possible at all or is only possible with a differing propagation velocity. In the case of acoustic waves their propagation in voids 4 is as well as completely prevented so that conclusions can be very clearly drawn about the fault 4 using the reflected waves (FIG. 10).

In the case of the electromagnetic waves and especially infrared light, the measuring device detects the various transitions or intersection planes 15, 16, 18 by interference and can thus draw conclusions about the layer thicknesses d1, d2, d3. The determination of layer thicknesses d1, d2, d3 takes place indirectly via the detection of peaks at the transitions 15, 16, 18 by interference. Based on the difference of these peaks the thickness of the respective layer which is limited by the transitions 15, 16, 18 can be computed. The evaluation unit automatically performs this computation. Here it must be noted that the measured layer thickness is linearly dependent on the index of refraction of the layer. This is because the electromagnetic waves propagate at different speeds in different materials, and the signal transit time through the layers linearly influences the location and/or the interval of the peaks which have been detected by the receiver 10. In one preferred embodiment, without corresponding correction the layer thickness measured for one layer seems higher for layers with higher index (n) of refraction by the factor of the index (n) of refraction.

For example, the measured layer thickness for an adhesive layer with a thickness d2 in the region of the adhesive would be d2*n, while the measured layer thickness in the region of possible voids which are located in the adhesive layer would be d2*1. This is based on the fact that air and vacuum have an index of refraction of roughly 1. The index of refraction (n) for different materials can be determined with methods which are known to one skilled in the art. Conventionally these values are also dependent on the wavelength of the electromagnetic signal used. For IR light with a wavelength of 1300 nm the index of refraction for current thermoplastic adhesives can be for example in the range between 1.2 and 2.5, but mostly between 1.3 and 2, but even more typically between 1.4 and 1.9.

In the measurement result for the adhesive layer thickness, the above described effects lead to an abrupt drop of the measured layer thickness (FIG. 7b, FIG. 7c) in the region of a void; this allows a conclusion about the void 4 by means of suitable evaluation algorithms. The X-axis of the figures/diagrams from FIGS. 7a to 7c constitutes the respective distance to the left edge of the wafer stack 8.

Figure 7A:
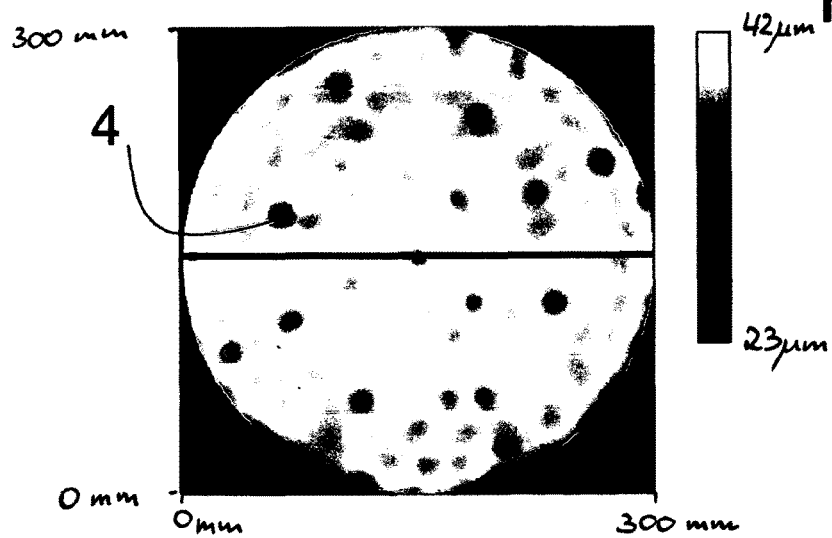
FIG. 7a shows a photograph of a wafer stack which has been sensed by infrared signals with the measuring device as claimed in the invention.
Figure 7B:
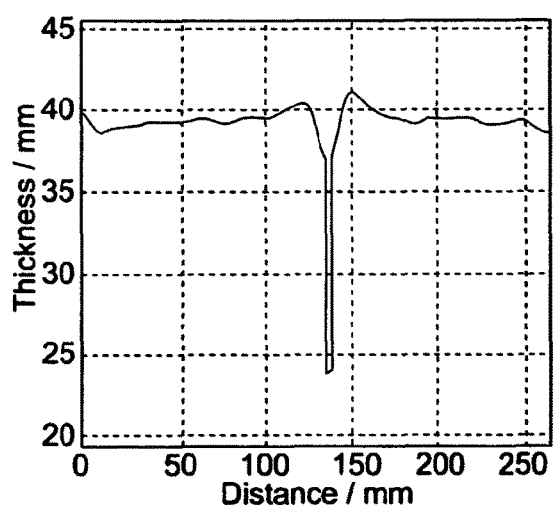
FIG. 7b shows a diagram of measurement and/or sensing of a wafer surface as claimed in the invention.
Figure 7C:
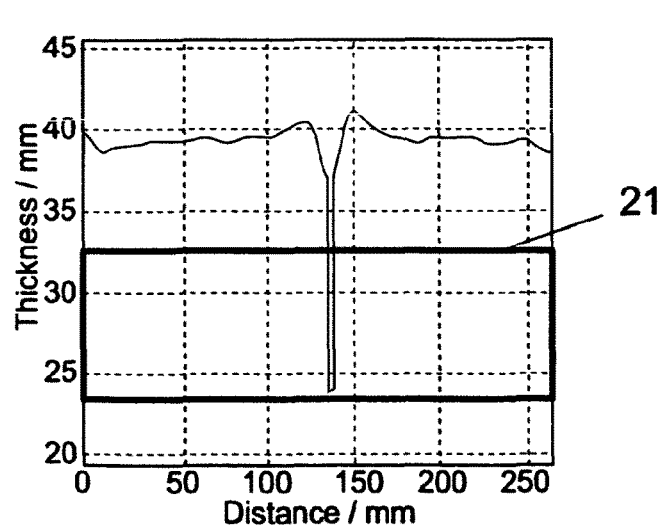
FIG. 7c shows a diagram of measurement and/or sensing of a wafer surface as claimed in the invention.

One example of the execution of an evaluation algorithm is shown by FIG. 7c. The evaluation unit is designed such that a freely definable window monitors a monitoring region 21 within the measurement region. If signals enter the monitoring region 21, a corresponding action is set. This is explained using one example. FIG. 7c constitutes the layer thickness d2 (thickness) of the connecting layer 2 as a function of the distance along the wafer stack 8. Apparently the layer thickness of the connecting layer 2 in this example varies between 37 and 42 µm. This thickness value in this case represents the value measured for the adhesive thickness without correction by the index of refraction. This means that the real adhesive thickness could be computed in this case by division of the illustrated thickness value by the index of refraction. In special embodiments it can be distinguished between bumps, dices, voids, bubbles, etc. They should be characterized by different depth/thickness/signal deviations. Here all corresponding algorithms are intended which can detect a signal deviation from the thickness. Advantageously, these evaluation algorithms are also combined with suitable algorithms which for example also consider the superficial extension of these voids. The superficial extension of the voids can be determined by an evaluation of all collected thickness values in the X/Y coordinate system according to the just described evaluation techniques. Possible intermediate values which have not been measured can advantageously be determined by interpolation.

For infrared measurement or ultrasonic measurement, the measurement and/or acquisition takes place independently of the distance R of the transmitter 9/receiver 10 from the wafer stack 8 since the measured values for the thicknesses of the individual layers take place by difference calculation based on the reflections on the individual transitions.

In order to be able to determine the thickness distribution of the individual layers to be measured over the entire wafer, it is necessary to accommodate a plurality of measuring points distributed over the wafer. Advantageously, the measuring points are arranged in a suitable coordinate system (see FIG. 10); this later facilitates the analysis and data processing. Advantageously, the coordinate system for measuring point acquisition corresponds to a local coordinate system which has been assigned to the wafer which is to be inspected. Suitable coordinate systems would for example be a Cartesian coordinate system or a polar coordinate system. Advantageously, the measuring points are placed close enough to one another to detect defects (voids) which can be typically expected with appropriate reliability. In particular it is desirable to detect defects of a size which would result in the above described catastrophic fault cases in the subsequent processing. The layer resolution should preferably be better than 10 µm, even more preferably better than 1 µm, most preferably better than 0.1 µm.

The diameter D of the measurement signal according to FIG. 10 is advantageously between 1 µm and 100 µm, preferably between 5 µm and 50 µm, and more preferably between 10 µm and 30 µm. For a laser beam the aforementioned diameter D corresponds for example to the diameter of the laser beam.

The width resolution of the measurement signal in the lateral direction, therefore parallel to the reference plane R, is between 0.1 µm and 50 µm, especially between 1 µm and 30 µm, preferably between 10 µm and 20 µm.

Analogously to the procedure with respect to voids, the wavelengths of the thickness fluctuation which typically occur are advantageously taken into account when the measuring point grid is fixed. Based on the above described considerations it has proven advantageous to set one measuring point roughly every 1 to 3 mm. In order to be able to more reliably recognize voids, it is even more ideal to set one measuring point every 0.8 mm or every 0.5 mm or even better every 0.25 mm. For especially sensitive applications with very small target wafer thicknesses it can also be advantageous to set one measuring point every 0.1 mm.

It is very often such that certain electromagnetic rays such as for example infrared are not able to penetrate the structure wafer 1 since it is either metal-coated, doped or bumped. Metal coatings can be present for example through contacts 14 on the structure wafer surface or within the structure wafer 1. The bumps 13 consist of metal coatings which are likewise opaque to IR. Furthermore the structure wafer 1 can be doped. Doping almost always occurs mainly in structure wafers and reduces the infrared transparency.

By means of an interferometer 19 which is integrated in addition to the measuring device 11 or into the measuring device 11 the surface 16 of the mount 12 can be measured before the wafer stack 8 is deposited on the mount 12. In FIG. 8 a surface unevenness of the mount surface 16 is represented by warpage. The irregularity of the surface can however have any other shape. This is measured with the white light interferometer 19. After measuring the distance profile by the white light interferometer 19 the wafer stack 8 is placed on the mount 12. Then the measurement is repeated by the white light interferometer 19 so that a second distance profile, specifically that of the entire wafer stack 8, is obtained. The difference of the two distance profiles corresponds to the total height of the wafer stack 8.

Thus, in combination with the above described measurement and/or detection of the transitions 15, 18 by corresponding computation, the layer thickness d3' can also be determined according to FIG. 8 by the layer thicknesses d1' of the wafer 3 and d2' of the connecting layer 2 being subtracted from the total thickness of the wafer stack 8.

Another advantage arises by using the white light interferometer as a scanner during the scan process by means of infrared or ultrasound. The white light interferometer scanner is moved only along one line beyond the edge of the wafer stack 8. Here it continuously measures the distance to the surface of the wafer stack 8 when it is located over it, or the distance to the mount surface 16 when it goes beyond the wafer stack 8. If at this point the height of the entire system changes during the actual infrared or ultrasonic scan, for example due to thermal fluctuations, the white light interferometer scanner detects this based on the fluctuation of the height since absolute distance can be determined. In contrast to the infrared scanner which measures by means of interference only the peaks which arise by interference on the interfaces 15, 16 and 18. The infrared scanner is therefore able to measure relative distances, therefore thicknesses. It always requires at least two signals from whose difference the thickness of the respective layer can be computed. The infrared scanner is therefore insensitive to "vibrations" and thermal fluctuations. The white light interferometer scanner conversely measures the distance to the transmitter-receiver unit. If its scan frequency over an entire scan line is much faster than the change in the height of the entire system, the change in the height of the entire system can be acquired as a function of time.

FIG. 7a shows a wafer stack 8 which is measured with a measuring device as claimed in the invention, with a diameter of 300 mm in which several voids 4 with a depth represented in color have been found. A two-dimensional evaluation of the wafer stack 8 according to FIG. 7a is done in FIG. 7b in the form of a diagram by the evaluation unit, the line corresponding to the diagram being drawn in FIG. 7a. It can be recognized in FIG. 7b how the void 4 in the middle of the wafer stack 8 appears in cross section.

Figure 11:
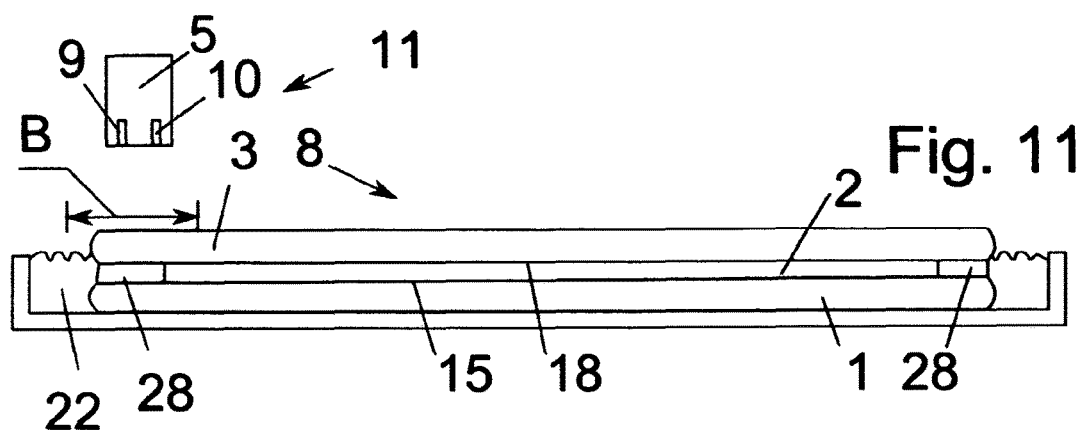
FIG. 11 shows a schematic of a device as claimed in the invention for processing of a wafer stack and FIG. 12 shows a measuring device as claimed in the invention in a fifth embodiment.

In another embodiment which is shown in FIG. 11, the edge zone B of the wafer stack 8 is measured in-situ by means of the above described measuring device during a chemical treatment process. Preferably the measurement method from FIG. 6c is used. While chemicals 22 dissolve an edge zone adhesive 28 of the connecting layer 2, the progress in the detachment process can be continuously measured by the measuring device 11. Advantageously the method is applied to wafer stacks 8 which bond the structure wafer 1 and the carrier wafer 3 only on the edge. These techniques are known to one skilled in the art in this field.

Figure 12:
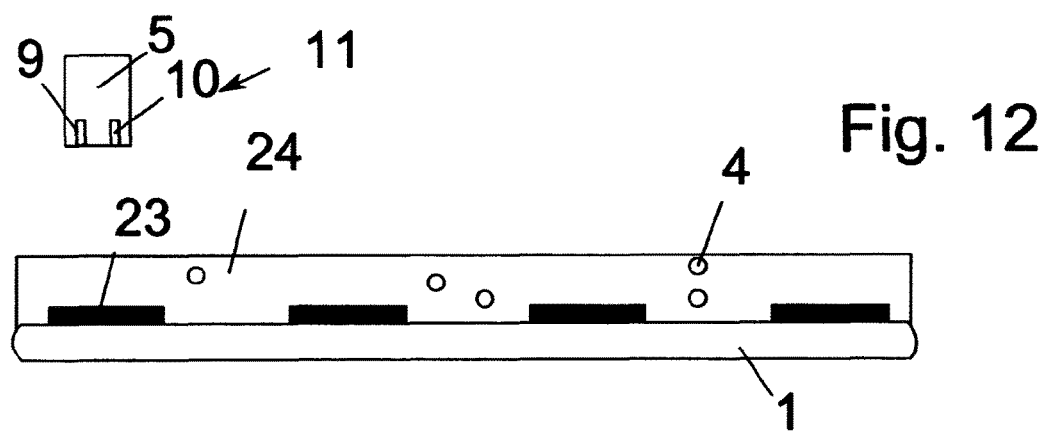

According to another embodiment which is shown in FIG. 12, voids 4 in a layer, especially a mold 24, which covers electronic components 23, especially dices, can be detected using the above described measuring device.

Doping elements which are preferred as claimed in the invention are elements of the third main group such as boron, indium, aluminum or gallium or elements of the fifth main group such as phosphorus, arsenic or antimony.

REFERENCE NUMBER LIST 1 structure wafer
2 connecting layer
3 wafer
4 voids
5 housing
6 membrane
7 liquid
8 wafer stack
9 transmitter
10 receiver
11 measuring device
12 mount
13 bumps
14 contacts
15 transition
16 mount surface
17 vacuum paths
18 transition
19 interferometer
20 measurement signal
21 monitoring region
22 chemicals
23 electronic components
24 layer
25 feed line
26 membrane wall
27 liquid reservoir
28 edge zone adhesive
R reference plane
d1, d1' layer thickness
d2, layer thickness
d3, d3' layer thickness
H distance
B edge zone

The invention claimed is:

1. A wafer processing device for processing a temporarily bonded wafer stack, comprising:
a temporary bonding device configured to temporarily bond layers to form the temporarily bonded wafer stack, said temporarily bonded layers comprising a structure wafer, a connecting layer of temporary adhesive, and a carrier wafer, the temporary bonding device being further configured to temporarily bond the structure wafer to the carrier wafer via the temporary adhesive connecting layer;
a measuring device configured to measure layer thicknesses and/or detect voids of one or more of the layers of the temporarily bonded wafer stack on a plurality of measuring points distributed on the temporarily bonded wafer stack, said measuring device comprising:
a housing configured to move relative to the temporarily bonded wafer stack;
a transmitter positioned within said housing in a bottom region thereof, said transmitter being configured to emit signals in the form of electromagnetic waves or ultrasonic waves into the temporarily bonded wafer stack,
a receiver positioned within said housing in the bottom region thereof proximate to said transmitter, said receiver being configured to receive signals that have been emitted by the transmitter and reflected on the temporarily bonded wafer stack, and
an evaluation unit configured to evaluate the signals that have been received by the receiver, distinguish a group of the signals reflected by at least two transitions between the layers of the temporarily bonded wafer stack, determine a distance of each signal of the group to one another and/or to a reference plane (R), and detect the movement of the temporarily bonded wafer stack and/or the device parallel to the reference plane (R) and a position of each measuring point along the reference plane (R),
a mount for accommodating and fixing the temporarily bonded wafer stack on one surface of the mount and for moving the fixed temporarily bonded wafer stack parallel to the reference plane (R), and
a debonding device configured to detach the temporarily bonded structure wafer from the carrier wafer.

2. A wafer processing device as claimed in claim 1, wherein the temporary bonding device, the measuring device, the debonding device, and the mount are disposed in an in-line system having a painting module for at least partial painting of the temporarily bonded wafer stack and an inspection module.

3. The device as claimed in claim 1, wherein the temporary adhesive connecting layer is positioned between the structure wafer and the carrier wafer to temporarily bond the structure wafer to the carrier wafer.

4. The device as claimed in claim 3, wherein the measured layer thickness of the temporary adhesive connecting layer is measured and/or voids in the temporary adhesive connecting layer are detected by the transmitter, the receiver, and the evaluation unit.

5. The device as claimed in claim 1, wherein the transmitter and the receiver are included in a transmitter-receiver unit, the transmitter-receiver unit being configured to move over an entirety of the wafer stack parallel to the reference plane (R) to scan the entirety of the wafer stack.

6. The device as claimed in claim 1, wherein the transmitter and the receiver are included in a transmitter-receiver unit, the transmitter-receiver unit being configured to scan the entirety of the wafer stack.

7. The device as claimed in claim 1, wherein the transmitter, the receiver, and the evaluation unit are configured to operate at a distance (H) from the temporarily bonded wafer stack.

8. The device as claimed in claim 1, wherein the transmitter and the receiver operate at the same time for measurement of the layer thicknesses and detection of the voids.

9. The device as claimed in claim 1, wherein adjacent ones of the measuring points with a distance less than 5 mm are measured.

10. The device as claimed in claim 1, wherein the transmitter, the receiver, and the evaluation unit are operated in-situ during a grinding process or a separating process.

11. The device as claimed in claim 1, further comprising an interferometer mechanically coupled and fixed to the transmitter and the receiver, the interferometer being configured to measure a distance from the interferometer to a surface of a mount on at least one of the measuring points.

12. The device as claimed in claim 1, wherein the transmitter and the receiver are aligned in a direction of the wafer stack parallel to the reference plane (R).

13. A wafer processing device for processing a temporarily bonded wafer stack, comprising:
a temporary bonding device configured to temporarily bond one or more layers to form the wafer stack, said layers comprising a structure wafer, a connecting layer of temporary adhesive, and a carrier wafer, the temporary bonding device being further configured to temporarily bond the structure wafer to the carrier wafer via the temporary adhesive connecting layer;
a measurement device arranged relative to a flat side of the wafer stack, the measurement device being configured to measure layer thickness and/or detect voids of the layers of the wafer stack at a plurality of measuring points distributed on the wafer stack, the measurement device comprising:
a housing configured to move relative to the wafer stack;
a transmitter positioned within said housing, said transmitter being configured to emit ultrasonic wave signals into the wafer stack; and
a receiver positioned within said housing proximate to said transmitter, said receiver being configured to receive signals that have been emitted by the transmitter and reflected on the wafer stack, evaluate the received signals, distinguish a group of the signals reflected by at least two transitions between the layers of the wafer stack, determine a distance of each signal of the group to one another and/or to a reference plane (R), and detect the movement of the wafer stack and/or the device parallel to the reference plane (R) and a position of each measuring point along the reference plane (R);
a mount for accommodating and fixing the wafer stack on one surface of the mount and for moving the fixed wafer stack parallel to the reference plane (R); and
a debonding device configured to detach the temporarily bonded structure wafer from the carrier wafer,
wherein the housing is further configured to immerse the transmitter and the receiver in a liquid applied to the wafer stack,
wherein the transmitter is further configured to emit the ultrasonic wave signals into the wafer stack while being immersed in the liquid by the housing, and
wherein the receiver is further configured to receive the reflected signals while being immersed in the liquid by the housing.

14. The device as claimed in claim 13, wherein the housing is further configured to apply the liquid to the wafer stack.

15. The device as claimed in claim 13, wherein the housing comprises a feed line through which the liquid is applied.

16. The device as claimed in claim 13, wherein the housing is further configured to apply the liquid to a membrane protecting the wafer stack from the liquid.

17. The device as claimed in claim 16, wherein the transmitter is further configured to inject the ultrasonic wave signals through the liquid and the membrane into the wafer stack.

18. A wafer processing device for processing a temporarily bonded wafer stack, comprising:
a temporary bonding device configured to temporarily bond one or more layers to form the wafer stack, said layers comprising a structure wafer, a connecting layer of temporary adhesive, and a carrier wafer, the temporary bonding device being further configured to temporarily bond the structure wafer to the carrier wafer via the temporary adhesive connecting layer;
a measurement device arranged relative to a flat side of the wafer stack, the measurement device being configured to measure layer thickness and/or detect voids of the layers of the wafer stack at a plurality of measuring points distributed on the wafer stack, the measurement device comprising:
a transmitter configured to inject electromagnetic or ultrasonic waves into the wafer stack; and
a receiver configured to receive signals created by reflection of the injected waves by the wafer stack, identify a group of the received signals that is reflected by at least two transitions between the layers of the wafer stack, determine a distance of each signal of the group to one another and/or to a reference plane (R), and detect movement of the wafer stack parallel to a reference plane (R) and a position of each measuring point along the reference plane (R) according to the movement of the wafer stack;
a mount configured to accommodate and fix the wafer stack on one surface of the mount and move the wafer stack parallel to the reference plane (R); and
a grinding wheel disposed in a separate space from the measurement device, the grinding wheel being configured to grind the wafer stack after the determination of the distance.

19. The device as claimed in claim 18, wherein the grinding wheel is further configured to grind the wafer stack after the detection of the movement and the position.

* * * * *